(12) United States Patent
Du

(10) Patent No.: US 12,144,618 B2
(45) Date of Patent: Nov. 19, 2024

(54) DEVICE AND METHOD FOR DETECTING SIGN PARAMETER

(71) Applicant: BOE Technology Group Co., Ltd., Beijing (CN)

(72) Inventor: Hui Du, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 742 days.

(21) Appl. No.: 17/416,326

(22) PCT Filed: Dec. 28, 2020

(86) PCT No.: PCT/CN2020/140196
§ 371 (c)(1),
(2) Date: Jun. 18, 2021

(87) PCT Pub. No.: WO2021/169551
PCT Pub. Date: Sep. 2, 2021

(65) Prior Publication Data
US 2022/0400982 A1    Dec. 22, 2022

(30) Foreign Application Priority Data
Feb. 24, 2020    (CN) .......................... 202010111869.9

(51) Int. Cl.
*A61B 5/1455*    (2006.01)
*A61B 5/00*    (2006.01)
*A61B 5/145*    (2006.01)

(52) U.S. Cl.
CPC ............ *A61B 5/1455* (2013.01); *A61B 5/002* (2013.01); *A61B 5/14546* (2013.01);
(Continued)

(58) Field of Classification Search
CPC . A61B 5/14546; A61B 5/1455; A61B 5/4848; A61B 5/7203; A61B 5/7235; A61B 5/7253; A61B 5/7275
See application file for complete search history.

(56) References Cited

U.S. PATENT DOCUMENTS 10,695,000 B2 *    6/2020    Bremer .............. A61B 5/14532
2003/0050541 A1    3/2003    Wuori
(Continued)

FOREIGN PATENT DOCUMENTS

CN    101647703 A    2/2010
CN    102217940 A    10/2011
(Continued)

OTHER PUBLICATIONS

CN202010111869.9 first office action.
CN202010111869.9 second office action.

*Primary Examiner* — Eric F Winakur
*Assistant Examiner* — Abel Seifu Abegaz
(74) *Attorney, Agent, or Firm* — IPro, PLLC

(57) ABSTRACT

A device and method for detecting a sign parameter are provided. A luminous source (01) is utilized to irradiate human skin tissue(s) for a preset time. The luminous source (01) can emit light with set wavelength(s) and capable of being absorbed by substance(s) for characterizing human body sign(s) in a human body. A photoelectric sensor (02) is configured to detect absorbance of the human body to the light emitted by the luminous source (01) within the preset time, and send a detection result to a processor (03). The processor (03) is configured to calculate substance concentration(s) of the substance(s) for characterizing the human body sign(s) in the human body according to the detection result sent by the photoelectric sensor (02). Therefore, blood samples of subjects do not need to be collected, and the (Continued)

substances for characterizing the human body signs can be detected through a non-invasive method.

10 Claims, 9 Drawing Sheets

(52) U.S. Cl.
CPC .......... *A61B 5/4848* (2013.01); *A61B 5/7203* (2013.01); *A61B 5/7235* (2013.01); *A61B 2560/0214* (2013.01)

(56) References Cited

U.S. PATENT DOCUMENTS

| | | | | |
|---|---|---|---|---|
| 2003/0060693 | A1* | 3/2003 | Monfre | A61B 5/1455 |
| | | | | 600/322 |
| 2017/0332951 | A1* | 11/2017 | Ahmad | G16H 50/20 |
| 2018/0020956 | A1 | 1/2018 | Lee et al. | |
| 2018/0317823 | A1 | 11/2018 | Khoja et al. | |
| 2018/0317825 | A1* | 11/2018 | Arfaoui | A61B 5/14532 |
| 2020/0390372 | A1* | 12/2020 | Workman | G01J 3/0264 |
| 2021/0113121 | A1* | 4/2021 | Diab | A61B 5/0073 |
| 2021/0235990 | A1 | 8/2021 | Eom et al. | |

FOREIGN PATENT DOCUMENTS

| | | | |
|---|---|---|---|
| CN | 105193423 | A | 12/2015 |
| CN | 105662434 | A | 6/2016 |
| CN | 105962949 | A | 9/2016 |
| CN | 106535763 | A | 3/2017 |
| CN | 106596416 | A | 4/2017 |
| CN | 109984727 | A | 7/2019 |
| CN | 111297374 | A | 6/2020 |

* cited by examiner

DEVICE AND METHOD FOR DETECTING SIGN PARAMETER

CROSS-REFERENCE TO RELATED APPLICATIONS

This application is the National Stage of International Application No. PCT/CN2020/140196, filed on Dec. 28, 2020, which claims the priority of the Chinese patent application No. 202010111869.9 filed with the China National Intellectual Property Administration on Feb. 24, 2020, the entire contents of which are incorporated herein by reference.

FIELD

This disclosure relates to the technical field of sign parameter detection, in particular to a device and method for detecting a sign parameter.

BACKGROUND

Blood is one of the most complex mixed liquids in nature, and is used to transport many molecules such as lipids, glucose, salts and proteins to all parts of a body. Blood flows through various tissues and organs of the human body, the change of blood composition has a significant impact on the realization of human function and tissue function, and the pathological changes of organisms also affect the blood compositions, so that it has great significance to analyze the blood. By detecting the content of various substances in the blood, the human health degree can be better monitored. For example, triacylglycerol can reflect the body fat content to a certain extent and is an index to diagnose obesity and coronary heart disease, while carbohydrates can reflect whether diet collocation is reasonable, and is also an index to diagnose diabetes.

At present, an invasive method is mainly adopted to detect the triacylglycerol and the carbohydrates, i.e., blood samples of subjects need to be obtained.

SUMMARY

Embodiments of the present disclosure provide a device and a method for detecting a sign parameter. The solution is as follows.

Embodiments of the present disclosure provide a device for detecting a sign parameter, including a luminous source, a photoelectric sensor, and a processor.

The luminous source is configured to adopt light, with a set wavelength and capable of being absorbed by a substance for characterizing a human body sign in a human body, to irradiate a human skin tissue for a preset time.

The photoelectric sensor is configured to detect absorbance of the human body to the light emitted by the luminous source within the preset time, and send a detection result to the processor.

The processor is configured to calculate a substance concentration of the substance for characterizing the human body sign in the human body according to the detection result sent by the photoelectric sensor.

Optionally, in the device for detecting the sign parameter provided by embodiments of the present disclosure, the substance for characterizing the human body sign includes triacylglycerol and carbohydrates.

Optionally, in the device for detecting the sign parameter provided by embodiments of the present disclosure, the processor is configured to:

conduct de-noising processing on the detection result sent by the photoelectric sensor, and extract waveform characteristic parameters in the processed result; and establish a fitting model by a partial least squares method according to the extracted waveform characteristic parameters, and calculate substance concentrations of the triacylglycerol and the carbohydrates in the human body.

Optionally, in the device for detecting the sign parameter provided by embodiments of the present disclosure, conducting by the processor the de-noising processing on the detection result sent by the photoelectric sensor, including:

conducting de-noising processing on the detection result sent by the photoelectric sensor by adopting a smoothing filtering method, a multiplicative scatter correction method, a standardized normal variate transformation method, and a fusion processing method.

Optionally, in the device for detecting the sign parameter provided by embodiments of the present disclosure, the processor is further configured to store the substance concentrations of the triacylglycerol and the carbohydrates obtained from each detection.

Optionally, the device for detecting the sign parameter provided by embodiments of the present disclosure further includes an evaluating system.

The evaluating system is configured to compare the substance concentrations of the triacylglycerol and the carbohydrates currently detected and stored in the processor with substance concentrations of the triacylglycerol and the carbohydrates previously stored and set as initial values to obtain a current change trend of the triacylglycerol and the carbohydrates.

Optionally, in the device for detecting the sign parameter provided by embodiments of the present disclosure, the evaluating system is further configured to evaluate a weight loss effect according to the current change trend of the triacylglycerol and the carbohydrates.

If the triacylglycerol and the carbohydrates both show a decreasing trend starting from the initial values, it is determined that weight loss is effective.

Optionally, the device for detecting the sign parameter provided by embodiments of the present disclosure further includes a wireless transmission module.

The wireless transmission module is configured to realize wireless transmission of data between the processor and the evaluating system.

Optionally, the device for detecting the sign parameter provided by embodiments of the present disclosure further includes a power module.

The power module is configured to supply power for the luminous source, the photoelectric sensor, the processor and the wireless transmission module.

Optionally, in the device for detecting the sign parameter provided by embodiments of the present disclosure, the set wavelength includes 4250 cm-1-4350 cm-1, 4450 cm-1-4550 cm-1, and 4550 cm-1-4650 cm-1.

Optionally, in the device for detecting the sign parameter provided by embodiments of the present disclosure, the set wavelength includes 4300 cm-1, 4500 cm-1, and 4600 cm-1.

Optionally, in the device for detecting the sign parameter provided by embodiments of the present disclosure, the waveform characteristic parameters at least include a wave crest value and a wave trough value.

Optionally, in the device for detecting the sign parameter provided by embodiments of the present disclosure, the preset time is greater than or equal to 5 minutes.

Accordingly, embodiments of the present disclosure further provide a method for detecting a sign parameter, including:

adopting light, with a set wavelength and capable of being absorbed by a substance for characterizing a human body sign in a human body, to irradiate a human skin tissue for a preset time;

detecting absorbance of the human body to the light emitted by a luminous source within the preset time; and calculating a substance concentration of the substance for characterizing the human body sign in the human body according to a detection result.

Optionally, in the method for detecting the sign parameter provided by embodiments of the present disclosure, the substance for characterizing the human body sign includes triacylglycerol and carbohydrates, and calculating the substance concentrations of the triacylglycerol and the carbohydrates in the human body according to the detection result, includes:

conducting de-noising processing on the detection result, and extracting waveform characteristic parameters in a processed result; and establishing a fitting model by a partial least squares method according to the extracted waveform characteristic parameters to calculate the substance concentrations of the triacylglycerol and the carbohydrates in the human body.

Optionally, in the method for detecting the sign parameter provided by embodiments of the present disclosure, conducting the de-noising processing on the detection result, includes:

conducting the de-noising processing on the detection result by adopting a smoothing filtering method, a multiplicative scatter correction method, a standardized normal variate transformation method, and a fusion processing method.

Optionally, in the method for detecting the sign parameter provided by embodiments of the present disclosure, after calculating the substance concentrations of the triacylglycerol and the carbohydrates in the human body according to the detection result, the method further includes:

storing the currently calculated substance concentrations of the triacylglycerol and the carbohydrates.

Optionally, the method for detecting the sign parameter provided by embodiments of the present disclosure, further includes:

comparing the stored and currently detected substance concentrations of the triacylglycerol and the carbohydrates with substance concentrations of the triacylglycerol and the carbohydrates previously stored and set as initial values to obtain a current change trend of the triacylglycerol and the carbohydrates.

Optionally, the method for detecting the sign parameter provided by embodiments of the present disclosure, further includes: evaluating a weight loss effect according to the current change trend of the triacylglycerol and the carbohydrates; and determining that weight loss is effective if the triacylglycerol and the carbohydrates both show a decreasing trend starting from the initial value.

DETAILED DESCRIPTION OF THE EMBODIMENTS

Figure 1:
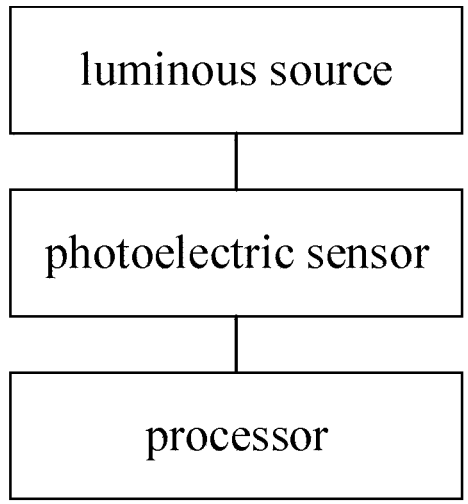
FIG. 1 is a schematic structural diagram of a sign parameter detection device provided by an embodiment of the present disclosure.

In order to make above objects, features and advantages of the present disclosure more obvious and understandable, the present disclosure will be further explained with reference to the drawings and embodiments. However, the exemplary embodiments can be implemented in a variety of forms and the present application should not be understood as being limited to the embodiments described herein. On the contrary, these embodiments are provided to make the present disclosure more comprehensive and complete, and to fully convey the concept of the exemplary embodiments to those skilled in the art. In the drawings, the same drawing reference numerals denote the same or similar structures, thus repeated description thereof will be omitted. Words expressing position and direction described in the present disclosure are illustrated by taking the attached drawings as an example, but they can also be changed as needed, and all the changes are included in the protection scope of the present disclosure. The drawings of the present disclosure are only used to illustrate the relative position relationship and do not represent the real scale.

It should be noted that specific details are described in the following description to facilitate a full understanding of the present disclosure. However, the present disclosure can be implemented in a variety of other ways different from those described herein, and those skilled in the art can make similar promotion without violating the connotation of the disclosure. Therefore, the present disclosure is not limited by specific embodiments disclosed below. The subsequent description of the specification is the preferred embodiments for implementing the present application, but the description is intended to explain the general principles of the present application and is not used to limit the scope of the present application. The scope of protection of the present application shall be defined by the appended claims.

A device and a method for detecting a sign parameter provided by embodiments of the present disclosure are described below with reference to the drawings.

Embodiment of the present disclosure provide a device for detecting a sign parameter, as shown in FIG. 1, including a luminous source 01, a photoelectric sensor 02, and a processor 03.

The luminous source 01 is configured to adopt light with set wavelength(s) and capable of being absorbed by substance(s) for characterizing human body sign(s) in a human body to irradiate human skin tissue for a preset time.

The photoelectric sensor 02 is configured to detect absorbance of the human body to the light emitted by the luminous source 01 within the preset time, and send a detection result to the processor 03.

The processor 03 is configured to calculate substance concentration(s) of the substance(s) for characterizing the human body sign(s) in the human body according to the detection result sent by the photoelectric sensor 02.

The device for detecting sign parameter(s) provided by embodiments of the present disclosure utilizes the luminous source to radiate the human skin tissue for the preset time. The luminous source can emit the light with the set wavelength(s) and capable of being absorbed by the substance(s) (e.g. triacylglycerol and carbohydrates) for characterizing the human body sign(s) in the human body. The photoelectric sensor is configured to detect the absorbance of the human body to the light emitted by the luminous source within the preset time, and send the detection result to the processor. The processor is configured to calculate the substance concentration(s) of the substance(s) for characterizing the human body sign(s) in the human body according to the detection result sent by the photoelectric sensor. Therefore, blood samples of subjects do not need to be collected, and the substance(s) for characterizing the human body sign(s) can be detected through a non-invasive method.

Optionally, in the device for detecting sign parameter(s) provided by embodiments of the present disclosure, the substances for characterizing the human body signs are mainly triacylglycerol and carbohydrates.

Optionally, in the device for detecting sign parameter(s) provided by embodiments of the present disclosure, the processor is configured to:
  conduct de-noising processing on the detection result sent by the photoelectric sensor, and extract waveform characteristic parameters in the detection result after being processed.
  establish a fitting model by a partial least squares method according to the extracted waveform characteristic parameters to calculate the substance concentrations of the triacylglycerol and the carbohydrates in the human body.

The processor firstly conducts de-noising processing on the detection result sent by the photoelectric sensor so as to remove an interference signal in the detection result obtained by the photoelectric sensor, so that the relatively ideal detection result is obtained.

In implementations, optionally, in the device for detecting sign parameter(s) provided by embodiments of the present disclosure, the processor conducts de-noising processing on the detection result sent by the photoelectric sensor, by:
  conducting the de-noising processing on the detection result sent by the photoelectric sensor by adopting a smoothing filtering method, a multiplicative scatter correction method, a standardized normal variate transformation method, and a fusion processing method so as to obtain a relatively ideal signal.

In implementations, the detection result after de-noising processing is generally in a periodically-changed waveform with wave crest and wave trough characteristics. Therefore, optionally, in the device for detecting sign parameter(s) provided by embodiments of the present disclosure, the waveform characteristic parameters include at least a wave crest value and a wave trough value.

Optionally, in the device for detecting sign parameter(s) provided by embodiments of the present disclosure, the processor is further configured to store the substance concentrations of the triacylglycerol and the carbohydrates obtained from each detection. Therefore, it is convenient for a user to check the substance concentrations of the triacylglycerol and the carbohydrates obtained from each detection in a later stage so as to judge the human body signs according to the substance concentrations of the triacylglycerol and the carbohydrates obtained from each detection.

Figure 2:
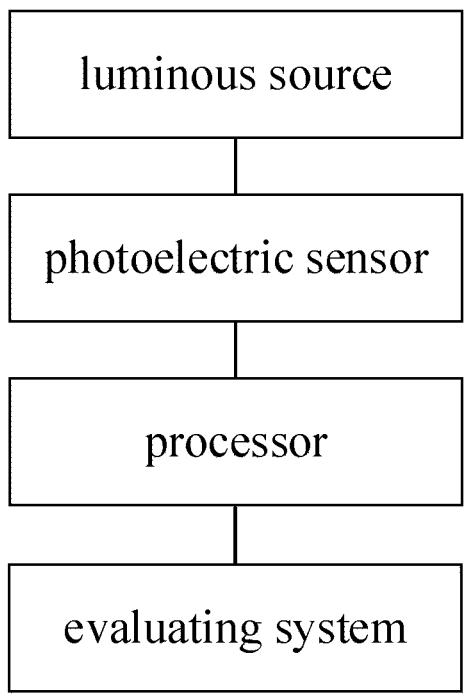
FIG. 2 is a schematic structural diagram of another sign parameter detection device provided by an embodiment of the present disclosure.

Optionally, the device for detecting sign parameter(s) provided by embodiments of the present disclosure, as shown in FIG. 2, further includes an evaluating system 04.

The evaluating system 04 is configured to compare the substance concentrations of the triacylglycerol and the carbohydrates currently detected and stored in the processor 03 with substance concentrations of the triacylglycerol and the carbohydrates previously stored and set as initial values to obtain a current change trend of the triacylglycerol and the carbohydrates.

In implementations, due to the fact that the intake of the triacylglycerol in the human body can reflect the accumulation amount of human fat in a period of time, the change trend of the triacylglycerol in a period of time can reflect the health condition of the human body. Therefore, the user can set the substance concentrations of the triacylglycerol and the carbohydrates obtained from first detection as the initial values which are used as reference values for subsequent measurement.

Furthermore, in implementations, the initial values can be reset after a period of time so as to avoid errors in the reference of the initial values at the present stage due to the facts that the time is too long and the body changes a lot.

Optionally, in the device for detecting sign parameter(s) provided by embodiments of the present disclosure, the evaluating system is further configured to evaluate a weight loss effect according to the current change trend of the triacylglycerol and the carbohydrates.

If both the triacylglycerol and the carbohydrates show a decreasing trend starting from the initial values, it is determined that weight loss is effective.

In implementations, weight loss is a gradual process and generally shows effect after a period of time. Therefore, generally, after the period of time, if the triacylglycerol is reduced by more than 5% and the carbohydrates are reduced by more than 15%, it can be determined that weight loss is effective.

In implementations, the change trend of the triacylglycerol and the carbohydrates may also be used as reference data in other aspects, such as rehabilitation reference data for obese patients, treatment reference data for patients with coronary heart disease, or reference for detecting whether dietary collocation of the patients is reasonable.

Figure 3:
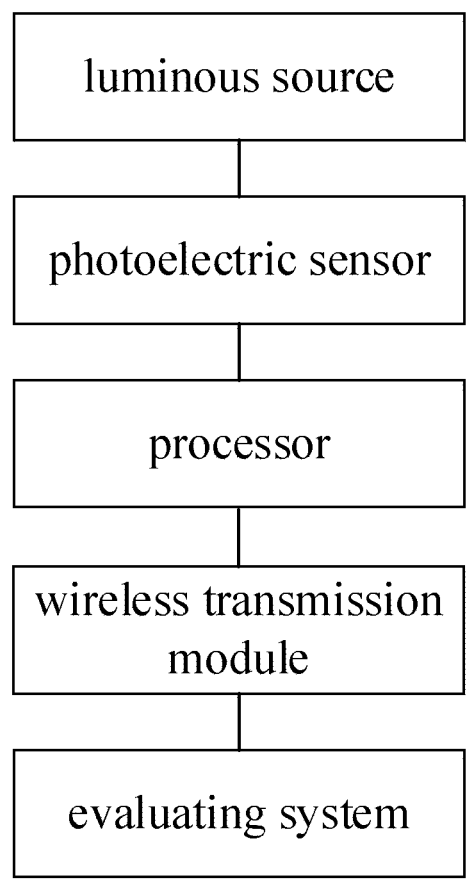
FIG. 3 is a schematic structural diagram of yet another sign parameter detection device provided by an embodiment of the present disclosure.

Optionally, the device for detecting sign parameter(s) provided by embodiments of the present disclosure, as shown in FIG. 3, further includes a wireless transmission module 05.

The wireless transmission module 05 is configured to realize wireless transmission of data between the processor 03 and the evaluating system 04.

In implementations, wireless transmission modes include: Bluetooth transmission, infrared transmission, near field communication (NFC) transmission, WiFi transmission and the like, which are not limited here.

Figure 4:
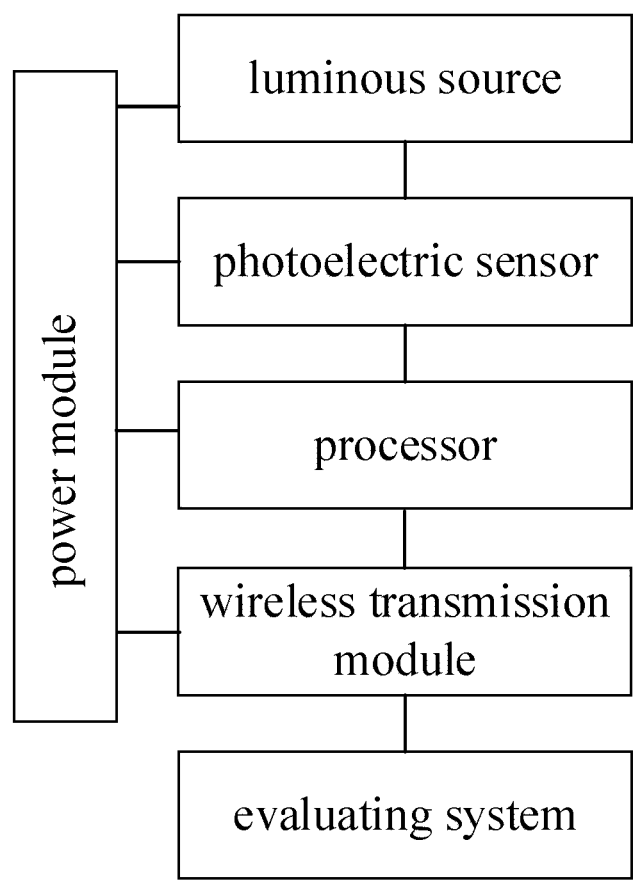
FIG. 4 is a schematic structural diagram of yet another sign parameter detection device provided by an embodiment of the present disclosure.

Optionally, the device for detecting sign parameter(s) provided by embodiments of the present disclosure, as shown in FIG. 4, further includes a power module 06. The power module 06 is configured to supply power for the luminous source 01, the photoelectric sensor 02, the processor 03 and the wireless transmission module 05.

Figure 5:
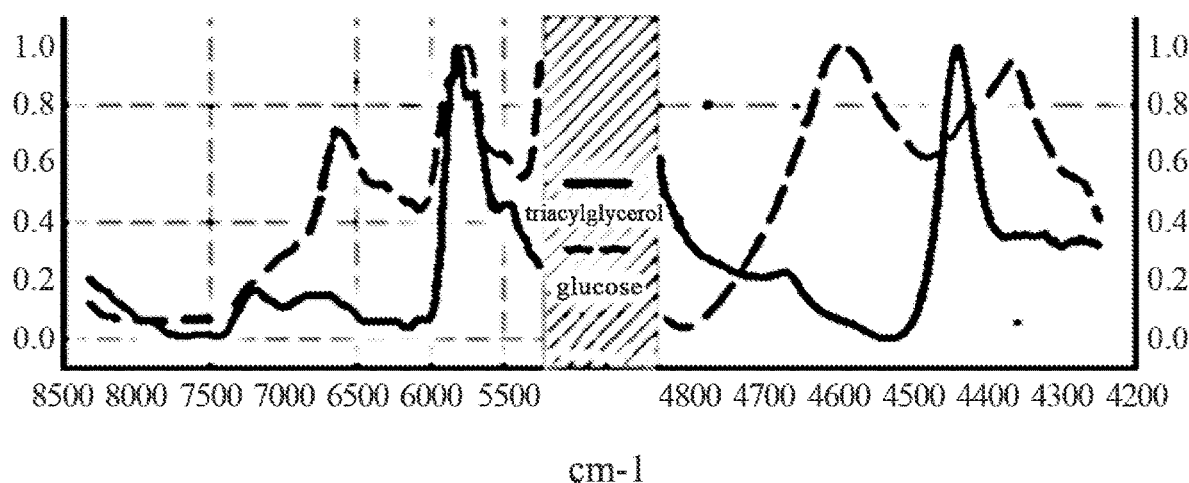
FIG. 5 is a curve diagram of transmittance of triacylglycerol and glucose.

In implementations, it is measured experimentally that a curve diagram of transmittance of the triacylglycerol and glucose is shown in FIG. 5. In FIG. 5, an ordinate represents the light transmittance. The greater the light transmittance is, the smaller the absorbance to the light is. Conversely, the smaller the light transmittance is, the greater the absorbance to the light is. The triacylglycerol has an obvious absorption peak when the light wavelengths are between 4450 cm-1-4550 cm-1 and between 5650 cm-1-5700 cm-1, and the glucose has an obvious absorption peak when the light wavelengths are between 4250 cm-1-4350 cm-1, between 4550 cm-1-4650 cm-1, and between 5650 cm-1-5700 cm-1. Due to mutual interference of the triacylglycerol and the glucose when the light wavelengths are between 5650-5700 $cm^{-1}$, optionally, according to the sign parameter detection device provided by embodiments of the present disclosure, the set wavelengths are: 4250 cm-1-4350 cm-1, 4450 cm-1-4550 cm-1, and 4550 cm-1-4650 cm-1.

It should be noted that cm-1=10000000/λ (nm). When the wavelength is 4300 cm-1, it represents that the wavelength λ=10000000/4300 (nm).

Further, in the device for detecting sign parameter(s) provided by embodiments of the present disclosure, the set wavelengths are about 4300 cm-1, 4500 cm-1, and 4600 cm-1. The glucose has the obvious absorption peak when the light wavelengths are about 4300 cm-1 and 4600 cm-1, and the triacylglycerol has the obvious absorption peak when the light wavelengths are about 4500 cm-1.

Specifically, in the device for detecting sign parameter(s) provided by embodiments of the present disclosure, due to the fact that contents of the triacylglycerol and the carbohydrates in blood are affected by pulse, heart beats, human actions and the like, it is necessary to determine the contents of the triacylglycerol and the carbohydrates according to the light absorbency of the triacylglycerol and the carbohydrates over a period of time.

Optionally, according to the device for detecting sign parameter(s) provided by embodiments of the present disclosure, duration of the preset time period is greater than or equal to 5 min.

Further, in the device for detecting sign parameter(s) provided by embodiments of the present disclosure, the luminous source can irradiate peripheral tissues of human skin, such as fingers and earlobes, where the light can penetrate through. The photoelectric sensor and the luminous source are respectively located on two sides of the peripheral tissues of the human skin. The photoelectric sensor detects the absorbance of the human body to the light emitted by the luminous source by receiving the light penetrating through the peripheral tissues of the human skin.

In implementations, when the human skin tissue is opaque, the photoelectric sensor and the luminous source are located on the same side of the human skin tissue. The photoelectric sensor detects the absorbance of the human body to the light emitted by the luminous source by receiving light reflected by the peripheral tissue of the human skin.

According to the sign parameter detection device provided by embodiments of the present disclosure, it should be noted that in order to reduce error, it is guaranteed to the greatest extent that the detection is carried out in the same state every time, for example, in a morning fasting state.

Figure 6:
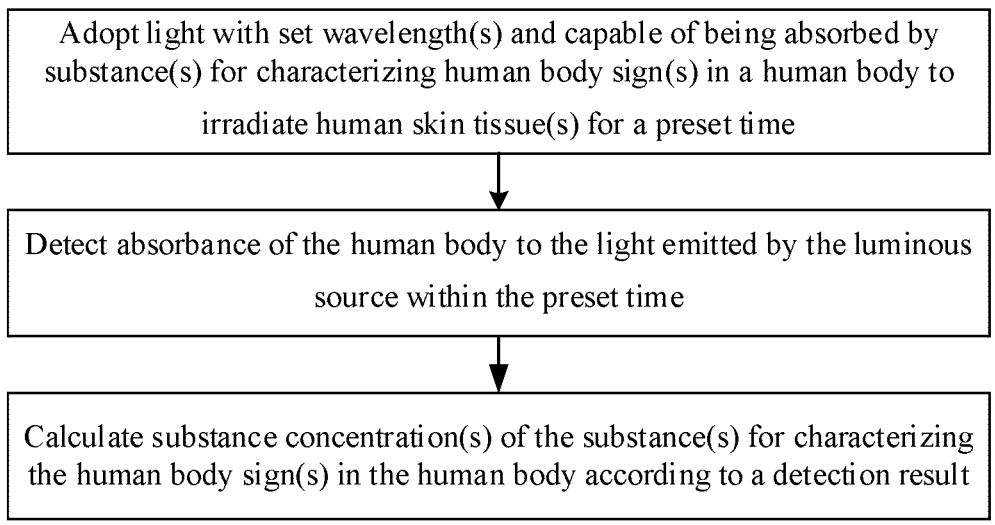
FIG. 6 is a flow chart of a method for detecting a sign parameter provided by an embodiment of the present disclosure.

Based on the same inventive concept, embodiments of the present disclosure further provide a method for detecting sign parameter(s), as shown in FIG. 6, including the following operations S101, S102, and S103.

S101, light with set wavelength(s) and capable of being absorbed by substance(s) for characterizing human body sign(s) in a human body is adopted to irradiate a human skin tissue for a preset time.

S102, absorbance of the human body to the light emitted by a luminous source within the preset time is detected.

S103, substance concentration(s) of the substance(s) for characterizing the human body sign(s) in the human body are calculated according to a detection result.

According to the method for detecting sign parameter(s) provided by embodiments of the present disclosure, the light with the set wavelength(s) and capable of being absorbed by the substance(s) for characterizing the human body sign(s) in the human body are adopted to irradiate the human skin tissue for the preset time, the absorbance of the human body to the light emitted by the luminous source within the preset time is detected, and the substance concentration(s) of the substance(s) for characterizing the human body sign(s) in the human body are calculated according to a detection result. Therefore, blood samples of subjects do not need to be collected, and the substances for characterizing the human body signs can be detected through a non-invasive method.

Optionally, in the detection method provided by embodiments of the present disclosure, the set wavelengths are 4250 cm-1-4350 cm-1, 4450 cm-1-4550 cm-1, and 4550 cm-1-4650 cm-1.

Optionally, according to the method for detecting sign parameter(s) provided by embodiments of the present disclosure, the set wavelengths are 4300 cm-1, 4500 cm-1, and 4600 cm-1.

Figure 7:
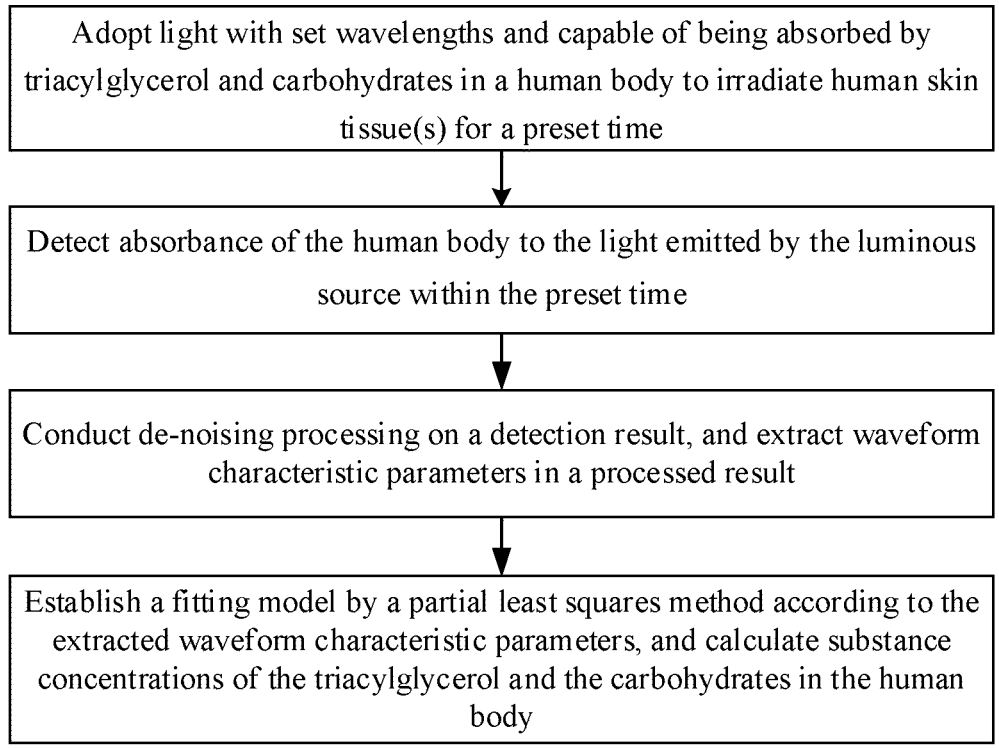
FIG. 7 is a flow chart of another method for detecting a sign parameter provided by an embodiment of the present disclosure.

Optionally, in the method for detecting sign parameter(s) provided by embodiments of the present disclosure, the substances for characterizing the human body signs are triacylglycerol and carbohydrates. As shown in FIG. 7, in step S103, calculating the substance concentrations of the substances for characterizing the human body signs in the human body according to the detection result includes the following operations S1031 and S1032.

S1031, de-noising processing is conducted on the detection result, and waveform characteristic parameters in a processed result are extracted.

S1032, a fitting model is established by a partial least squares method according to the extracted waveform characteristic parameters to calculate the substance concentrations of the triacylglycerol and the carbohydrates in the human body.

Optionally, in the method for detecting sign parameter(s) provided by embodiments of the present disclosure, conducting the de-noising processing on the detection result includes the following operation.

The de-noising processing is conducted on the detection result by adopting a smoothing filtering method, a multiplicative scatter correction method, a standardized normal variate transformation method, and a fusion processing method.

Figure 8:
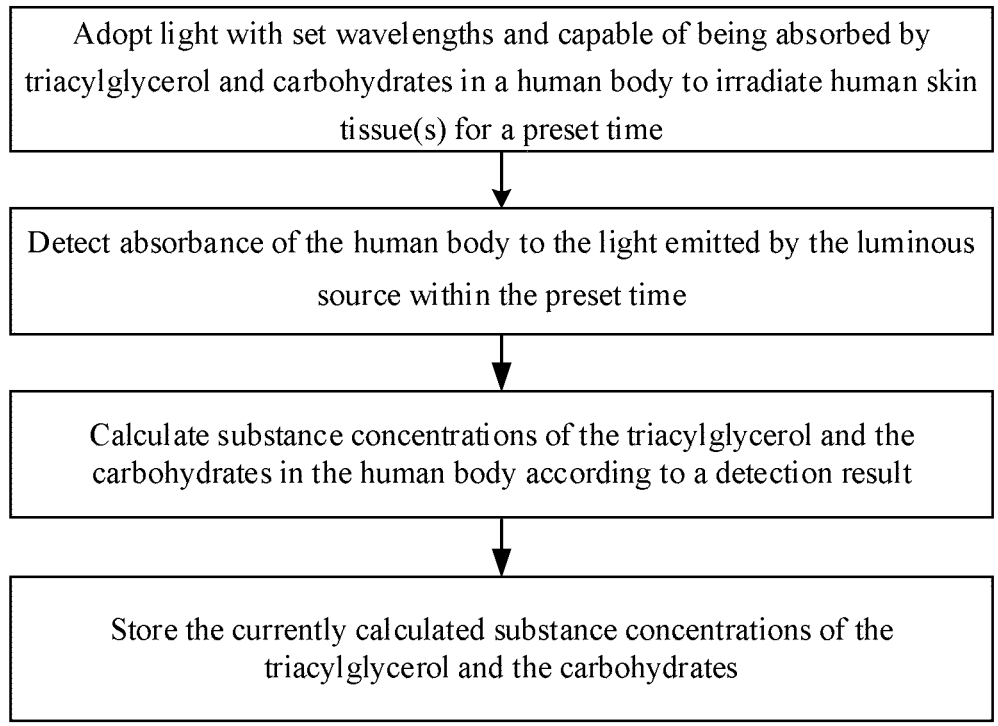
FIG. 8 is a flow chart of yet another method for detecting a sign parameter provided by an embodiment of the present disclosure.

Optionally, in the method for detection sign parameter(s) provided by embodiments of the present disclosure, as shown in FIG. 8, after step S103 of calculating the substance concentrations of the triacylglycerol and the carbohydrates in the human body according to the detection result, the method further includes the following operation S104.

S104, the currently detected substance concentrations of the triacylglycerol and the carbohydrates are stored.

Figure 9:
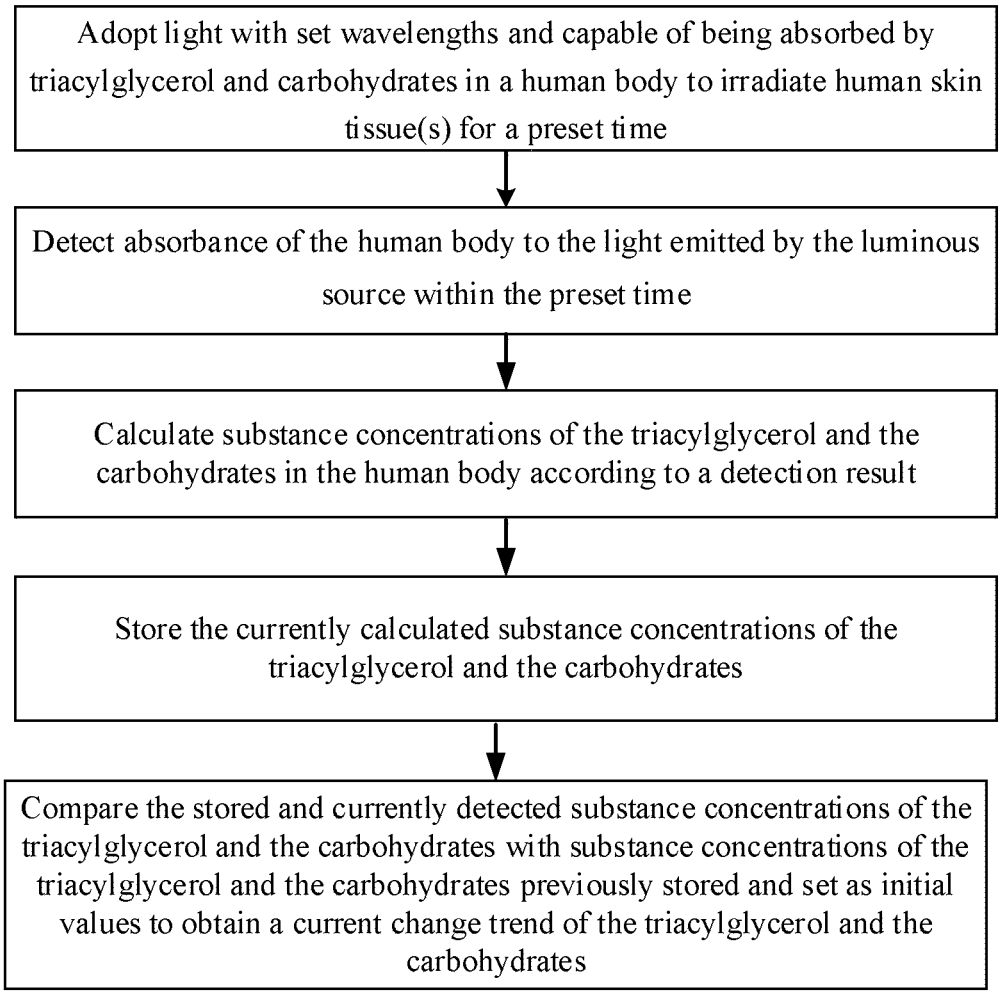
FIG. 9 is a flow chart of yet another method for detecting a sign parameter provided by an embodiment of the present disclosure.

Optionally, the sign parameter detection method provided by embodiments of the present disclosure, as shown in FIG. 9, further includes the following operation S105.

S105, the stored and currently detected substance concentrations of the triacylglycerol and the carbohydrates are compared with substance concentrations of the triacylglycerol and the carbohydrates previously stored and set as initial values to obtain a current change trend of the triacylglycerol and the carbohydrates.

Figure 10:
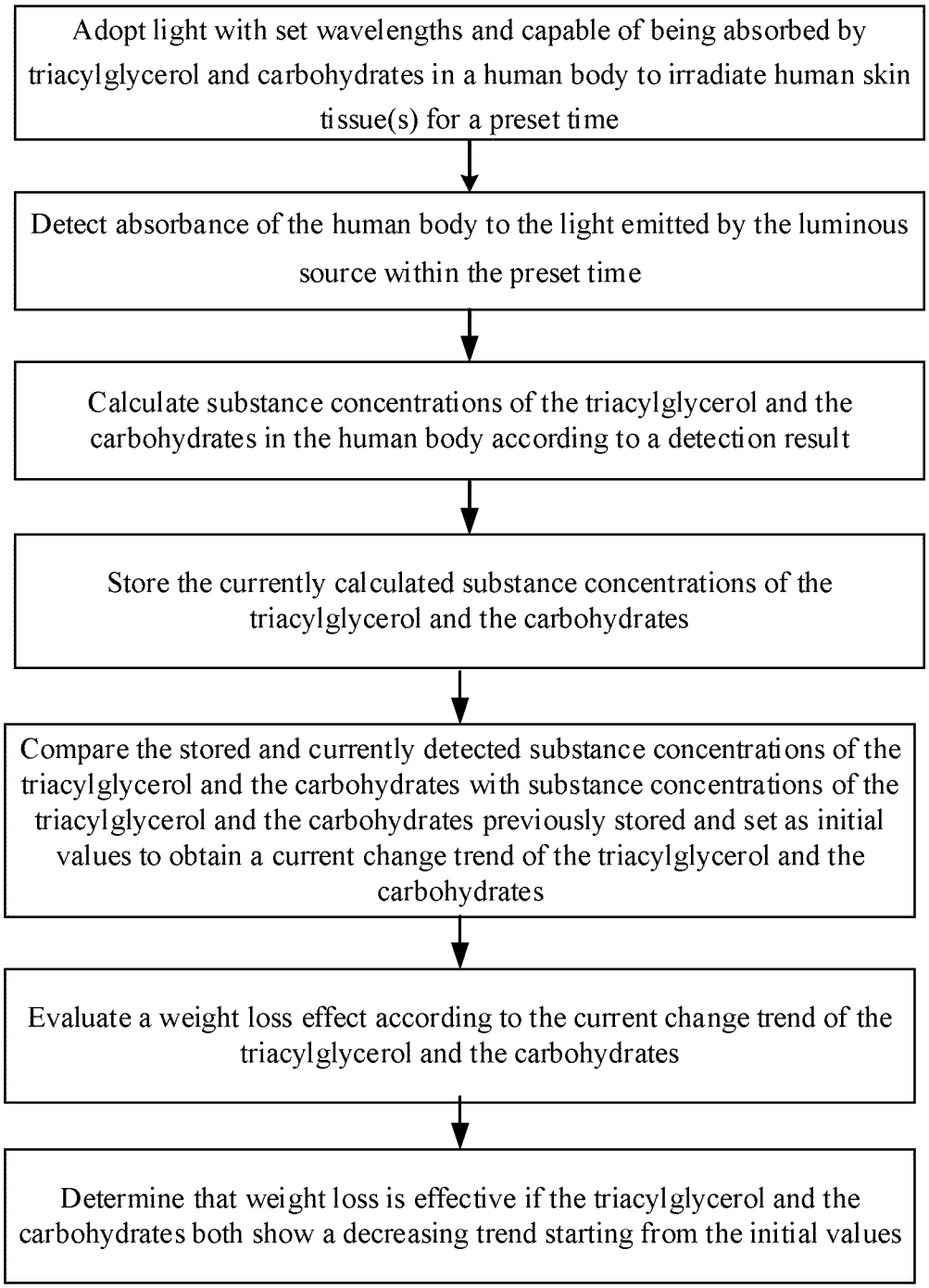
FIG. 10 is a flow chart of yet another method for detecting a sign parameter provided by an embodiment of the present disclosure.

Optionally, the sign parameter detection method provided by the embodiment of the present disclosure, as shown in FIG. 10, further includes the following operations S106 and S107.

S106, a weight loss effect is evaluated according to the current change trend of the triacylglycerol and the carbohydrates.

S107, if both the triacylglycerol and the carbohydrates show a decreasing trend starting from the initial values, it is determined that weight loss is effective.

Optionally, in the sign parameter detection method provided by embodiments of the present disclosure, the waveform characteristic parameters at least include a wave crest value and a wave trough value.

According to the above sign parameter detection device and the sign parameter detection method provided by the embodiments of the present disclosure, the luminous source is utilized to irradiate the human skin tissue for the preset time. The luminous source can emit the light with the set wavelengths and capable of being absorbed by the substances (such as the triacylglycerol and the carbohydrates) for characterizing the human body signs in the human body. The photoelectric sensor is configured to detect the absorbance of the human body to the light emitted by the luminous source within the preset time, and send the detection result to the processor. The processor is configured to calculate the substance concentrations of the substances for characterizing the human body signs in the human body according to the detection result sent by the photoelectric sensor. Therefore, the blood samples of the subjects do not need to be collected, and the substances for characterizing the human body signs can be detected through the non-invasive method.

Obviously, those skilled in the art may make various changes and transformations for the present disclosure without departing from the spirit and scope of the present disclosure. In this case, if these changes and transformations of the present disclosure belong to the scope of claims of the present disclosure and their equivalent technologies, the present disclosure is also intended to include these changes and transformations.

What is claimed is:

1. A device for detecting a sign parameter, comprising:
a luminous source configured to emit light, capable of being absorbed by a substance for characterizing a vital sign of a human body in the human body, to irradiate a human skin tissue for a preset time, wherein the substance for characterizing the vital sign of the human body comprises triacylglycerol and carbohydrates;
a photoelectric sensor configured to:
detect absorbance of the human body to the light emitted by the luminous source within the preset time, and
send a detection result to a processor;
the processor configured to:
conduct de-noising processing on the detection result sent by the photoelectric sensor;
extract waveform characteristic parameters in the detection result after being de-noising processed;
establish a fitting model by a partial least squares method according to the extracted waveform characteristic parameters;
calculate substance concentrations of the triacylglycerol and the carbohydrates in the human body; and
store the substance concentrations of the triacylglycerol and the carbohydrates obtained from each detection; and
an evaluating system configured to:
obtain a current change trend of the triacylglycerol and the carbohydrates by comparing the substance concentrations of the triacylglycerol and the carbohydrates currently detected and stored in the processor with substance concentrations of the triacylglycerol and the carbohydrates previously stored and set as initial values; and
evaluate a weight loss effect according to the current change trend of the triacylglycerol and the carbohydrates;
wherein when both the triacylglycerol and the carbohydrates show a decreasing trend starting from the initial values, it is determined that weight loss is effective.

2. The device for detecting the sign parameter according to claim 1, wherein said conducting by the processor the de-noising processing on the detection result sent by the photoelectric sensor, comprises:
conducting the de-noising processing on the detection result sent by the photoelectric sensor by a fusion of a smoothing filtering method, a multiplicative scatter correction method, and a standardized normal variate transformation method.

3. The device for detecting the sign parameter according to claim 1, further comprising:
a wireless transmission module configured to realize wireless transmission of data between the processor and the evaluating system.

4. The device for detecting the sign parameter according to claim 3, further comprising:
a power module configured to supply power for the luminous source, the photoelectric sensor, the processor and the wireless transmission module.

5. The device for detecting the sign parameter according to claim 1, wherein a wavenumber of the light is in ranges of 4250 $cm^{-1}$-4350 $cm^{-1}$, 4450 $cm^{-1}$-4550 $cm^{-1}$, or 4550 $cm^{-1}$-4650 $cm^{-1}$.

6. The device for detecting the sign parameter according to claim 5, wherein the wavenumber is 4300 $cm^{-1}$, 4500 $cm^{-1}$, or 4600 $cm^{-1}$.

7. The device for detecting the sign parameter according to claim 1, wherein the waveform characteristic parameters at least comprise a wave crest value and a wave trough value.

8. The device for detecting the sign parameter according to claim 1, wherein the preset time is greater than or equal to 5 minutes.

9. A method for detecting a sign parameter, comprising:
emitting light capable of being absorbed by a substance for characterizing a vital sign of a human body in the human body, to irradiate a human skin tissue for a preset time, wherein the substance for characterizing the vital sign of the human body comprises triacylglycerol and carbohydrates;

detecting absorbance of the human body to the light emitted by a luminous source within the preset time;

conducting de-noising processing on a result of the detecting;

extracting waveform characteristic parameters in the result after being de-noising processed;

establishing a fitting model by a partial least squares method according to the extracted waveform characteristic parameters;

calculating the substance concentrations of the triacylglycerol and the carbohydrates in the human body;

storing the currently calculated substance concentrations of the triacylglycerol and the carbohydrates;

comparing the stored and currently detected substance concentrations of the triacylglycerol and the carbohydrates with substance concentrations of the triacylglycerol and the carbohydrates previously stored and set as initial values, to obtain a current change trend of the triacylglycerol and the carbohydrates;

evaluating a weight loss effect according to the current change trend of the triacylglycerol and the carbohydrates; and determining that weight loss is effective when both the triacylglycerol and the carbohydrates show a decreasing trend starting from the initial values.

10. The method for detecting the sign parameter according to claim 9, wherein said conducting the de-noising processing on the result of the detecting, comprises:

conducting the de-noising processing on the result of the detecting by a fusion of a smoothing filtering method, a multiplicative scatter correction method, and a standardized normal variate transformation method.

* * * * *